United States Patent

Sato et al.

[11] 4,219,219
[45] Aug. 26, 1980

[54] DEVELOPERS FOR PRESSURE-SENSITIVE RECORDING AND DEVELOPING SHEETS CONTAINING THEM

[75] Inventors: Kozo Sato, Minami-ashigara; Hajime Kato, Fujinomiya, both of Japan

[73] Assignee: Fuji Photo Film Co., Ltd., Minami-ashigara, Japan

[21] Appl. No.: 17,862

[22] Filed: Mar. 5, 1979

[30] Foreign Application Priority Data

Mar. 6, 1978 [JP] Japan ................... 53-25158

[51] Int. Cl.² .................. B41M 5/16; B41M 5/22
[52] U.S. Cl. ................... 282/27.5; 106/21; 427/150; 427/151; 428/307; 428/914
[58] Field of Search ............ 106/21; 282/27.5; 427/150, 151, 152, 153; 428/307, 411, 537, 913, 914; 560/71, 143; 562/477

[56] References Cited

U.S. PATENT DOCUMENTS

| | | | |
|---|---|---|---|
| 3,864,146 | 2/1975 | Oda et al. | 282/27.5 |
| 3,924,027 | 12/1975 | Saito et al. | 427/147 |

*Primary Examiner*—Bruce H. Hess

*Attorney, Agent, or Firm*—Sughrue, Rothwell, Mion, Zinn and Macpeak

[57] ABSTRACT

In a pressure sensitive recording sheet comprising a layer of microcapsules containing a color former and a color developer, said layer of microcapsules and said color developer being on the same or independent supports, the improvement which comprises said developer being a polyvalent metal salt of a substituted salicylic acid represented by the general formulae (I) or (II):

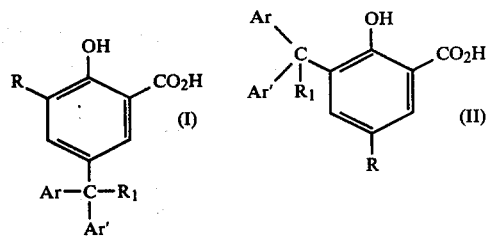

wherein R represents a hydrogen atom, an alkyl group, an aralkyl group or an aryl group, $R_1$ represents a hydrogen atom, an alkyl group, an aryl group or an aralkyl group and Ar and Ar' which may be the same or different each represents an aryl group.

9 Claims, No Drawings

DEVELOPERS FOR PRESSURE-SENSITIVE RECORDING AND DEVELOPING SHEETS CONTAINING THEM

BACKGROUND OF THE INVENTION

1. Field of the Invention

The present invention relates to developers for pressure-sensitive recording and to developing sheets containing the same. In greater detail, the present invention relates to novel developers for pressure-sensitive recording which comprise a polyvalent metal salt of salicyclic acid substituted by a 1,1-diarylalkyl group or a triarylmethyl group and developing sheets containing the same.

2. Description of the Prior Art

A pressure-sensitive recording system in practical use at the present time comprises microcapsules containing in solution a colorless or slightly colored electron donating dye precursor (hereinafter, a "color former") and an electron attracting material (hereinafter, a "developer") as described for example in U.S. Pat. Nos. 2,712,507, 2,730,456 and 2,730,457. Formation of developed images is accomplished by contacting the color former contained in a dissolved state in the microcapsules with the developer upon destruction or rupture of the capsules.

Hitherto, though clay minerals such as acid clay, attapulgite or bentonite, etc., phenols and phenol-formaldehyde resins have been used as developers, they all suffer several serious defects. For example, the developing ability of clay minerals deteriorates with time and the light fastness and water resistance of the developed images are poor. The developing ability of the phenols is low and their stability with time is poor. Further, phenol-formaldehyde novolak resins have low developing ability for couplers such as leuco Auramine type couplers or spiropyran type couplers, etc., and they produce images which are easily yellowed by light and the light fastness of the developed images is poor.

Recently, it has been reported in Japanese Patent Publications Nos. 10,856/74 and 25,174/76 and U.S. Pat. No. 3,934,070 that polyvalent metal salts of salicylic acid derivatives are excellent developers. Of these developers, however, the metal salts of salicylic acids having low oil-solubility and low molecular weight do not exhibit good stability to hydrolysis (i.e., there is a reduction in their developing ability resulting from hydrolysis of the metal salts to form free acids), they can be developed by water (e.g., color formation takes place when wetted as the color former contacts the developer surface) and they suffer a deterioration in developing ability with time, etc. Further, with salicylic acid derivatives having 12 or more carbon atoms having a large oil-solubilizing group (described in Japanese Patent Publication No. 25,174/76), though the above described defects are somewhat overcome, the developing ability and definition of the developed images are not adequate, and thus developers having higher developing ability have been required. For example, zinc 4-pentadecylsalicylate and zinc 5-octadecylsalicylate have insufficient developing ability.

SUMMARY OF THE INVENTION

An object of the present invention is to provide novel developers for pressure-sensitive recording which have good developing ability and excellent water resistance, heat resistance and light fastness and which form developed images having excellent water resistance, light fastness and stability with time.

The object of the present invention has been attained using (i) developers comprising a polyvalent metal salt of a substituted salicylic acid represented by the following general formula (I) or (II) and (ii) developers comprising a polyvalent metal salt of a substituted salicylic acid represented by the following general formula (I) or (II) and one or more oxides, hydroxides, carbonates or carboxylic acid salts of zinc, aluminum, titanium, silicon, boron, magnesium and calcium or inorganic pigments such as activated clay, kaolin, talc and the like:

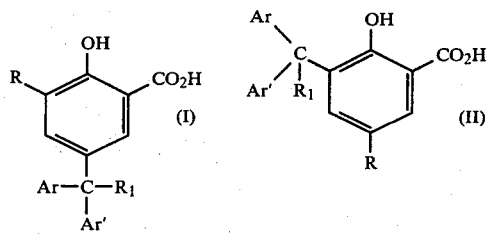

wherein R represents a hydrogen atom, an alkyl group, an aralkyl group or an aryl group, $R_1$ represents a hydrogen atom, an alkyl group, an aralkyl group or an aryl group and Ar and Ar' which may be the same or different, each represents an aryl group.

DETAILED DESCRIPTION OF THE INVENTION

The term alkyl group used herein includes straight or branched chain alkyl groups and cycloalkyl groups.

Preferably, R represents a hydrogen atom, a straight or branched chain alkyl group having 1 to 8 carbon atoms (such as a methyl group, an isopropyl group, a tert-butyl group, etc.), a cycloalkyl group having 5 to 8 carbon atoms (such as a cyclohexyl group, etc.), an aralkyl group having 7 to 9 carbon atoms (such as a benzyl group, a phenethyl group, etc.) or an aryl group having 6 to 10 carbon atoms (such as a phenyl group, etc.).

Preferably, $R_1$ represents a hydrogen atom, an alkyl group having 1 to 5 carbon atoms (such as a methyl group, an ethyl group, an n-butyl group, etc.) or an aryl group having 6 to 10 carbon atoms (such as a phenyl group or an alkyl substituted phenyl group having 7 to 10 carbon atoms, e.g., a tolyl group, an ethylphenyl group, a p-isopropylphenyl group, a xylyl group, etc.).

Ar and Ar', which may be the same or different, each represents an aryl group having 6 to 18 carbon atoms (such as a phenyl group, an alkyl substituted phenyl group having 7 to 10 carbon atoms, e.g., a tolyl group, an ethylphenyl group, a p-isopropylphenyl group, a xylyl group, etc., a naphthyl group, an alkyl substituted naphthyl group having 11 to 18 carbon atoms, e.g., a methyl-1-naphthyl group, an isopropyl-1-naphthyl group, a di-isopropylnaphthyl group, etc.).

It is particularly preferred that R is a hydrogen atom, a methyl group, a cyclohexyl group or a phenyl group; $R_1$ is an alkyl group having 1 to 4 carbon toms (such as a methyl group, an ethyl group, an n-butyl group, etc.), a phenyl group or an alkyl substituted phenyl group having 7 to 10 carbon atoms (such as a tolyl group, a p-isopropylphenyl group, a xylyl group, etc.), and Ar and Ar', which may be the same or different are an alkyl substituted phenyl group having 7 to 10 carbon atoms (such as a tolyl group, an ethylphenyl group, a p-isopropylphenyl group, a xylyl group, etc.).

Polyvalent metal salts of substituted salycylic acids have been synthesized in which various oil solubilizing groups have been introduced. When the properties of these developers are examined, polyvalent metal salts of 1,1-diarylalkylsalicylic acids or triarylmethylsalicylic acids represented by the above described formula (I) or (II) not only have two great advantages that they have good developing ability and the developed images are very sharp. In addition they are excellent in other properties required of a developer, for example, stability with time, water resistance, and light fastness and water resistance of developed images, etc. Further, they exhibit very excellent developing property without water development. It is believed that these properties are highly influenced by and to a large extent the product of the 1,1-diarylalkyl group or triarylmethyl group which is the oil-solubilizing group.

The metal salts of 1,1-diarylalkylsalicylic acids or triarylmethylsalicylic acids of the present invention exhibit particularly excellent results when Crystal Violet lactone is used as the color former because they form pure blue developed images which are fast and very bright in comparison to Crystal Violet lactone images formed with prior art developers.

Examples of 1,1-diarylalkylsalicylic acids and triarylmethylsalicylic acids represented by the general formulas (I) and (II) of the present invention are set forth below, however, the present invention is not limited to the salts of these compounds.

(1)—3-Diphenylmethylsalicylic acid.
(2)—5-Diphenylmethylsalicylic acid.
(3)—3-(1,1-Diphenylethyl)salicylic acid.
(4)—5-(1,1-Diphenylethyl)salicylic acid.
(5)—3-(Di-p-tolylmethyl)salicylic acid.
(6)—5-(Di-p-tolylmethyl)salicylic acid.
(7)—3-[Di-(p-ethylphenyl)methyl]salicylic acid.
(8)—5-[Di-(p-ethylphenyl)methyl]salicylic acid.
(9)—3-[Di-(p-isopropylphenyl)methyl]salicylic acid.
(10) 5-[Di-(p-isopropylphenyl)methyl]salicylic acid.
(11)—3-Dixylylmethylsalicylic acid.
(12)—5-Dixylylmethylsalicylic acid.
(13)—5-Triphenylmethylsalicylic acid.
(14)—5-Tritolylmethylsalicylic acid.
(15)—5-Tri-(ethylphenyl)methylsalicylic acid.
(16)—5-Tri-(p-isopropylphenyl)methylsalicylic acid.
(17)—5-Trixylylmethylsalicylic acid.
(18)—5-Dinaphthylmethylsalicylic acid.
(19)—5-Di-(isopropylnaphthyl)methylsalicylic acid.
(20)—3-Methyl-5-diphenylmethylsalicylic acid.
(21)—3-Methyl-5-(1,1-diphenylethyl)salicylic acid.
(22)—3-Methyl-5-[Di-(p-tolyl)methyl]salicylic acid.
(23)—3-Methyl-5-[Di-(p-ethylphenyl)methyl]salicylic acid.
(24)—3-Methyl-5-[Di-(p-isopropylphenyl)methyl]salicylic acid.
(25)—3-Methyl-5-triphenylmethylsalicylic acid.
(26)—3-Methyl-5-triphenylmethylsalicylic acid.
(27)—3-Methyl-5-tritolylmethylsalicylic acid.
(28)—3-Methyl-5-trixylylmethylsalicylic acid.
(29)—3-Methyl-5-dinaphthylmethylsalicylic acid.
(30)—5-(Diphenyl-p-tolylmethyl)salicylic acid.
(31)—5-(Di-p-tolyl-phenylmethyl)salicylic acid.
(32)—5-(Diphenylxylylmethyl)salicylic acid.
(33)—5-(Dixylylphenylmethyl)salicylic acid.
(34)—5-(Diphenyl-p-ethylphenylmethyl)salicylic acid.
(35)—5-[Diphenyl-(p-isopropylphenyl)methyl]salicylic acid.

The various properties of the substituted salicylic acids represented by the general formulae (I) and (II) required for attaining the objects of the present invention are improved by converting their carboxyl group into a polyvalent metal salt, for example, the developing ability remarkably increases. The polyvalent metals which can form the developer salts in the present invention include metals such as magnesium, calcium, aluminum or tin, etc. and transition metals such as titanium, vanadium, chromium, manganese, iron, cobalt, nickel, copper or zinc, etc. Among them, zinc and aluminum salts are preferred because they have excellent development properties, they are inexpensive and form colorless salts. Particularly, zinc salts are useful because of their high developing ability.

If the polyvalent metal salts of the substituted salicylic acids represented by the general formulae (I) and (II) are used together with one or more oxides, hydroxides, carbonates and carboxylic acid (aromatic or aliphatic, monobasic or dibasic having 1 to 18 carbon atoms) salts of zinc, aluminum, titanium, silicon, boron, magnesium and calcium or an inorganic pigment such as activated clay, kaolin, talc and the like, a synergistic effect is brought about, by which the developing ability, the stability to the lapse of time and the light fastness of the developed images are further improved. Among the metal compounds it is preferred to use zinc oxide, aluminum hydroxide, silicon dioxide, aluminum silicate, activated clay, zinc naphthanate and zinc 2-ethylhexanoate in combination with the metal salicylates of the acids of formulae (I) and (II). Suitable amounts of the oxides, hydroxides, carbonates and carboxylic acid salts are about 0.1 to about 100, preferably 0.5 to 20 parts, more preferably 1 to 6 parts by weight per part by weight of the salicylic acid derivative. A suitable amount of inorganic pigment is about 0.1 to about 100 parts, preferably 0.5 to 50 parts, more preferably 1 to 20 parts by weight per part by weight of the developer.

Hereafter, processes for synthesizing the 1,1-diarylalkyl salicylic acids and triarylmethylsalicylic acids of the present invention and the metal salts thereof are described.

The substituted salicylic acids represented by the general formula (I) or (II) of the present invention are obtained by (1) a Kolbe-Schmitt reaction of the corresponding 1,1-diarylalkylphenols or triarylmethylphenols or (2) 1,1-diarylalkylation or triarylmethylation of salicylic acid. Conversion of the free acids into polyvalent metal salts is generally carried out by reacting a sodium, potassium or ammonium salt of the corresponding acids with a water soluble salt, generally, a chloride or sulfate, of the polyvalent metal in water. However, dehydration reaction which comprises heating the free acid and a hydroxide, oxide or carbonate of the polyvalent metal has also been used.

SYNTHESIS EXAMPLE 1

Zinc 5-triphenylmethylsalicylate, Compound (13)

75.2 g (0.8 mol) of phenol and 52 g (0.2 mol) of triphenylcarbinol were boiled by heating on an oil bath and the resulting water was gradually removed together with excess phenol. When generation of water stopped, the reaction mixture was cooled to about 100° C. by allowing it to stand. Thereafter 2 g of zinc chloride was added and the mixture was heated to 130° to 140° C. whereupon white crystals rapidly precipitated. After heating for 30 minutes, the mixture was allowed to cool and 100 ml of methanol was added thereto, and the crystals were separated by filtration to obtain 51 g of p-triphenylmethylphenol having a melting point of 293° to 295° C.

40 g (0.119 mol) of p-triphenylmethylphenol, 120 g of anhydrous potassium carbonate and 80 ml of dimethylformamide were placed in an autoclave. Thereafter carbon dioxide gas was introduced so as to produce a pressure of 40 kg/cm$^2$, the mixture was stirred at 170° C. for 6 hours. After cooling, 500 ml of water was added to the contents of the autoclave, by which the potassium 5-triphenylmethylsalicylate, Compound (13), precipitated, which was then separated by filtration and washed with water. The yield was 50 g which is nearly stoichiometric.

The free acid of the compound (13) (m.p.: 218°-220° C.) was obtained by acidifying the above described potassium salt with hydrochloric acid. 41.8 g (0.1 mol) of the potassium salt of compound (13), 17.25 g (0.06 mol) of zinc sulfate (7H$_2$O) and 1 liter of water were vigorously stirred at 80° C. for 6 hours to convert the potassium salt of compound (13) into the zinc salt. After being allowed to cool, white crystals were separated by filtration and washed with water to obtain 40 g of the zinc 5-triphenylmethylsalicylate.

SYNTHESIS EXAMPLE 2

Zinc 3-diphenylmethylsalicylate, Compound (1)

A mixture of 20 g (0.145 mol) of salicylic acid, 20 g (0.109 mol) of benzhydrol, 20 g (0.105 mol) of p-toluenesulfonic acid and 200 ml of acetic acid was refluxed for 1 hour with heating. After being allowed to cool, acetic acid was removed by distillation under reduced pressure and the resulting crystals were separated by filtration and washed with acetic acid and water to obtain 24.5 g of crude product. By the recrystallization of the crude product using a mixture of benzene and hexane, 3-diphenylmethylsalicylic acid [Compound (1), melting point 194°-196° C.] was obtained.

12.2 g (0.04 mol) of 3-diphenylmethylsalicylic acid, Compound (1), was dissolved in 200 ml of water in which 1.6 g (0.04 mol) of sodium hydroxide had been dissolved. To the resulting solution, a solution prepared by dissolving 6.9 g (0.024 mol) of zinc sulfate heptahydrate in 100 ml of water was added. After stirring at room temperature for 1 hour, the resulting white crystals were separated by filtration and washed with water to obtain 12.9 g of zinc 3-diphenylmethylsalicylate.

SYNTHESIS EXAMPLE 3

Zinc 5-diphenylmethylsalicylate, Compound (2)

A mixture of 25 g (0.182 mol) of salicylamide, 30 g (0.163 mol) of benzhydrol, 30 g (0.158 mol) of p-toluenesulfonic acid and 200 ml of acetic acid was refluxed for 3 hours with heating. After cooling, the precipitated white crystals were separated by filtration and washed with water to obtain 5-diphenylmethylsalicylamide. Thereafter 40 g of sodium hydroxide in 100 ml of water were added and the mixture was heated on a steam bath for 6 hours with stirring. After being allowed to cool, the mixture was acidified using diluted hydrochloric acid to obtain 40 g of a crude product comprising 5-diphenylmethylsalicylic acid, Compound (2). When the crude product was recrystallized using diluted methanol, it had a melting point of 190° to 191.5° C. The resulting Compound (2) was converted into the zinc salt by the same process as that described in Synthesis Example 2.

SYNTHESIS EXAMPLE 4

Zinc 5-(phenylditolylmethylsalicylate, Compound (31)

p-(Phenyl-di-tolylmethyl)phenol was synthesized in the same manner as in Synthesis Example 1 using phenyl-di-tolylcarbinol obtained by reacting benzotrichloride with toluene in the presence of aluminium chloride. The phenol was then subjected to carboxylation by the Kolbe reaction in the same manner as in Synthesis Example 1 to produce the corresponding salicylic acid. The resulting Compound (31) was converted into the zinc salt according to the process described in Synthesis Example 2.

SYNTHESIS EXAMPLE 5

Zinc 3-methyl-5-triphenylmethyl salicylate, Compound (26)

2-Methyl-4-(triphenylmethyl)phenol was synthesized by the same process as described in Synthesis Example 1 except that o-cresol was used instead of phenol. It was then subjected to carboxylation by Kolbe reaction in the same manner as in Synthesis Example 1 to obtain 3-methyl-5-triphenylmethylsalicylic acid, Compound (26). This compound was converted to the zinc salt by the same process as in Synthesis Example 1.

SYNTHESIS EXAMPLE 6

Zinc 5-(1,1-diphenylethyl)salicylate, Compound (4)

1,1-Diphenylethylene and phenol in an excess amount were heated in an oil bath at 140° to 150° C. for 1 hour in the presence of p-toluenesulfonic acid. After being allowed to cool, p-toluenesulfonic acid was neutralized using sodium hydrogencarbonate and the excess phenol was then removed by steam distillation to obtain p-(1,1-diphenylethyl)phenol. The resulting phenol was then subjected to carboxylation by the Kolbe reaction according to the process described in Synthesis Example 1 to obtain Compound (4) which was then converted into the zinc salt by the same process as that described in Synthesis Example 2.

In order to produce a developing sheet containing the polyvalent metal salts of substituted salicylic acids represented by the general formula (I) or (II) in the present invention, at least one of the above described polyvalent metal salts was applied to a support, for example, paper, synthetic paper, non-woven fabrics, etc., together with, if necessary, a binder such as gum arabic, ethylcellulose, carboxymethylcellulose, polyvinyl alcohol or a latex such as, for example, styrene-butadiene copolymer, styrene-maleic acid anhydride copolymer, etc. using a solvent. As the solvent, though water is generally and conveniently used, various organic solvents, for example, ethyl acetate, acetone, benzene or toluene, etc., can be used.

Application of the developer coating solution can be carried out by typical application methods, for example, by a blade coater, an air knife coater, a wire wound bar coater, a size press coater, a roll coater, a gravure coater, or a flexo coater, etc. The examination of the properties for the developers of the present invention was carried out using developing sheets prepared by using a coating rod.

It is possible to apply the developer and microcapsules containing a solution of a color former to the same support.

The developing sheets using the developers of the present invention have adequate developing ability and other developing properties can be satisfied using the developers in amounts much smaller than the prior clay coating paper. Namely, in prior art clay coated paper about 7 to 10 g/m² clay is required. On the contrary for the developing sheets of the present invention it is sufficient to apply the polyvalent metal salts of substituted salicylic acids represented by the general formulae (I) and (II) in amounts of only about 0.1 to 1 g/m² and preferably 0.3 to 0.5 g/m².

The developing sheets of the present invention can be used in combination with conventional microcapsule sheets. These microcapsule sheets have been described in, for example, U.S. Pat. Nos. 2,800,457, 2,800,458, 3,190,837, 3,341,466 and 4,001,140 and Japanese Patent Publications Nos. 24,782/64 and 16,166/72. Microcapsules used for them are conveniently produced by a coacervation process, an interfacial polycondensation process, an in situ process, a process for drying in liquid or an insolubilizing process, etc. As the color formers used for these microcapsules, there are, for example, Crystal Violet lactone, Malachite Green lactone, Benzoyl leuco Methylene Blue, Rhodamine B Lactam, 3-dibenzylamino-7-diethylaminofluoran and 3-methyl-2,2'-spirodinaphthopyran, 2-methyl-3-anilino-7-diethylaminofluoran, etc. with Crystal Violet lactone, Rhodamine B lactam, dibenzylamino-7-diethylaminofluoran, 2-methyl-3-anilino-7-diethylaminofluoran, etc. being particularly preferred. These color formers may be used in combination. For example, a combination of Rhodamine B lactam and 3-dibenzylamino-7-diethylaminofluoran may be used.

The developing sheets using the polyvalent metal salts of substituted salicylic acids represented by the general formulae (I) and (II) are not only used as pressure-sensitive recording paper but can also be used in heat-sensitive recording described in, for example, German Patent Application (OLS) No. 1,919,397, etc.

In the following Example, the present invention is further illustrated.

EXAMPLE

Process (1) for producing developing sheets

A coating solution prepared by dissolving 10 g of the zinc salt of 5-triphenylmethylsalicylic acid (13) in 100 ml of ethyl acetate was applied to base paper (40 g/m²) using a coating rod so as to provide 0.4 g/m² of the zinc salt, and dried to obtain a developing sheet (I). Developing sheets (II), (III), (IV), (V) and (VI) were produced in the same manner except that the zinc salt of 3-diphenylmethylsalicylic acid (1), the zinc salt of 5-diphenylmethylsalicylic acid (2), the zinc salt of 5-[di-(p-tolyl)phenylmethyl]salicylic acid (31), the zinc salt of 3-methyl-5-triphenylmethylsalicylic acid (26) and the zinc salt of 5-(1,1-diphenylethyl)salicylic acid (4) were used instead of the zinc salt of the above described acid (13).

Process (2) for producing a developing sheet

A coating solution prepared by finely dispersing 10 g of zinc salt of 5-triphenylmethylsalicylic acid (13) and 2 g of ethyl cellulose in 100 ml of water was applied to base paper (40 g/m²) using a coating rod so at to provide 0.4 g/m² of the zinc salt of 5-triphenylmethylsalicylic acid (13) and dried to obtain a developing sheet (VII).

Process (3) for producing a developing sheet 10 g of zinc salt of 5-triphenylmethylsalicylic acid (13), 2 g of zinc oxide and 2 g of ethyl cellulose were finely dispersed in 100 ml of water. The resultant dispersion was applied to a base paper in the same manner as process (2) and dried to obtain a developing sheet (VIII).

Process (4) for producing a developing sheet 10 g of zinc salt of 5-triphenylmethylsalicylic acid (13), 2 g of zinc oxide and 2 g of aluminium hydroxide were finely dispersed in 100 ml of water to produce a coating solution. It was applied to base paper in the same manner as in process (1) and dried to obtain a developing sheet (IX).

Process for producing comparison developing sheets

Comparison developing sheets (X), (XI) and (XII) were produced in the same manner as in process (1), except that zinc 4-pentadecylsalicylate, zinc 3,5-di-($\alpha$-methylbenzyl)salicylate and phenol-formaldehyde novolak resin were used instead of the zinc salt of 5-triphenylmethylsalicylic acid (13).

A microcapsule sheet containing Crystal Violet lactone as a color former was placed on the resulting developing sheets I through XII and 600 kg/cm² of the load pressure was applied thereto to form developed images. After being allowed to stand in the dark for 1 hour, reflection spectra of the developed images were measured. The density at the absorption maximum (610 nm) was used as a measure of developing ability of the developing sheet. Further, the microcapsule sheets used for this examination were produced by the coacervation process described in U.S. Pat. No. 2,800,457. The results are set forth in the following Table.

Table

| Developing Sheet No. | Metal Salt of Substituted Salicylic Acid | Metal Salt used in Combination | Solvent for Application | Developing Ability (density) |
|---|---|---|---|---|
| I | Zinc salt of 5-triphenylmethylsalicylic acid (13) | — | Ethyl acetate | 0.50 |
| II | Zinc salt of 3-diphenylmethylsalicylic acid (1) | — | Ethyl acetate | 0.48 |
| III | Zinc salt of 5-diphenylmethylsalicylic acid (2) | — | Ethyl acetate | 0.46 |
| IV | Zinc salt of 5-(ditolylphenylmethyl)- | — | Ethyl acetate | 0.52 |

Table-continued

| Developing Sheet No. | Metal Salt of Substituted Salicylic Acid | Metal Salt used in Combination | Solvent for Application | Developing Ability |
|---|---|---|---|---|
| | salicylic acid (31) | | | |
| V | Zinc salt of 3-methyl-5-triphenylmethyl-salicylic acid (26) | — | Ethyl acetate | 0.52 |
| VI | Zinc salt of 5-(1,1-diphenylethyl)-salicylic acid (4) | — | Ethyl acetate | 0.51 |
| VII | Zinc salt of 5-triphenylmethylsalicylic acid (13) | — | Water | 0.42 |
| VIII | Zinc salt of 5-triphenylmethylsalicylic acid (13) | Zinc oxide | Ethyl acetate | 0.47 |
| IX | Zinc salt of 5-triphenylmethylsalicylic acid (13) | Zinc oxide and aluminum hydroxide | Ethyl acetate | 0.48 |
| X | Zinc 4-pentadecyl-salicylate | — | Ethyl acetate | 0.15 |
| XI | Zinc 3,5-di-(α-methylbenzyl)salicylate | — | Ethyl acetate | 0.38 |
| XII | Phenol-formaldehyde novolak resin (available on the market) | — | Ethyl acetate | 0.31 |

The developing sheets (I to IX) containing the developers of the present invention have excellent developing ability as compared with the developing sheets for comparison (X to XII). Further, the developing sheets (VIII) and (IX) in which water is used as the solvent have high developing ability as a result of the combined effect of the metal salt.

Moreover, in developing sheets (I) to (IX) of the present invention, the developed images have a very brilliant pure blue color. However, with the developing sheet for comparison (XI), the developed images have a somewhat reddish blue color, which is not preferred for practical use.

While the invention has been described in detail and with reference to specific embodiments thereof, it will be apparent to one skilled in the art that various changes and modifications can be made therein without departing from the spirit and scope thereof.

What is claimed is:

1. In a pressure-sensitive recording material comprising a support having coated thereon a developer and a layer of microcapsules containing a color former coated on the same or an independent support, the improvement which comprises: said developer being a polyvalent metal salt of a substituted salicylic acid represented by the following general formula (I) or (II)

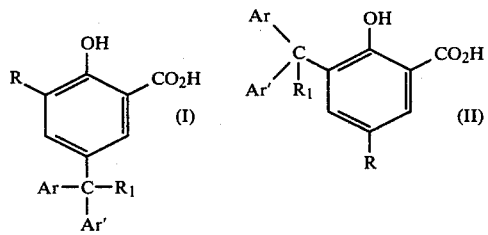

wherein R represents a hydrogen atom, an alkyl group, an aralkyl group or an aryl group, R₁ represents a hydrogen atom, an alkyl group, an aryl group or an aralkyl group, and Ar and Ar' which may be the same or different each represents an aryl group.

2. The pressure-sensitive recording material of claim 1, wherein said developer additionally comprises one or more of an oxide, hydroxide, carbonate or carboxylic acid salt of zinc, aluminum, titanium, boron, silicon, magnesium or calcium, as an essential ingredient, where said carboxylic acid salt is other than a substituted salicylic acid represented by the general formula (I) or (II) of claim 1.

3. The pressure-sensitive material of claims 1 or 2, wherein R represents a hydrogen atom, a straight chain or branched chain alkyl group having 1 to 8 carbon atoms, a cycloalkyl group having 5 to 8 carbon atoms, an aralkyl group having 7 to 9 carbon atoms, or an aryl group having 6 to 10 carbon atoms; $R_1$ represents a hydrogen atom, an alkyl group having 1 to 4 carbon atoms, or an aryl group having 6 to 10 carbon atoms, and Ar and Ar', which may be the same or different, each represents an aryl group having 6 to 18 carbon atoms.

4. The pressure-sensitive material of claims 1 or 2, wherein R represents a hydrogen atom, a methyl group, a cyclohexyl group, or a phenyl group; $R_1$ represents an alkyl group having 1 to 4 carbon atoms, a phenyl group or an alkyl substituted phenyl group having 7 to 10 carbon atoms, and Ar and Ar', which may be the same or different, each represents an alkyl substituted phenyl group having 7 to 10 carbon atoms.

5. The pressure-sensitive material of claims 1 or 2, wherein said polyvalent metal of said salt of said substituted salicylic acid represented by the general formula (I) or (II) is a metal selected from the group consisting of magnesium, calcium, aluminum, tin, titanium, vanadium, chromium, manganese, iron, cobalt, nickel, copper and zinc.

6. The pressure-sensitive material of claim 5, wherein said polyvalent metal is zinc or aluminum.

7. The pressure-sensitive material of claim 2, wherein said metal oxide, hydroxide, carbonate or carboxylic acid salt is selected from the group consisting of zinc oxide, aluminum hydroxide, silicon dioxide and aluminum silicate.

8. The pressure-sensitive material of claim 2, wherein said oxide, hydroxide, carbonate or carboxylic acid is present in an amount of about 0.1 to about 100 parts by weight per part by weight of said salt of a substituted salicylic acid represented by the general formula (I) or (II).

9. The pressure-sensitive recording material of claim 1 or 2, wherein said color former is selected from the group consisting of Crystal Violet Lactone, Rhodamine B Lactam, dibenzylamino-7-diethylaminofluoran and 2-methyl-3-anilino-7-diethylaminofluoran.

* * * * *